(12) United States Patent
Rønborg et al.

(10) Patent No.: US 6,447,482 B1
(45) Date of Patent: Sep. 10, 2002

(54) INJECTOR

(75) Inventors: Steen Meier Rønborg, Bagsværd (DK); Claus Møllsøe, Bagsværd (DK)

(73) Assignee: Claus Mollsoe, Bagsvaerd (DK)

( * ) Notice: Subject to any disclaimer, the term of this patent is extended or adjusted under 35 U.S.C. 154(b) by 210 days.

(21) Appl. No.: 09/614,980

(22) Filed: Jul. 12, 2000

Related U.S. Application Data

(63) Continuation of application No. PCT/DK99/00005, filed on Jan. 5, 1999.

Foreign Application Priority Data

Jan. 12, 1998 (DK) .......................................... 1998 0031

(51) Int. Cl.$^7$ .............................................. A61M 37/00
(52) U.S. Cl. ..................................... 604/131; 600/556
(58) Field of Search ................................ 604/131, 511, 604/156, 207, 135, 195, 134, 136, 196; 600/583, 556

(56) References Cited

U.S. PATENT DOCUMENTS

| | | | | |
|---|---|---|---|---|
| 4,304,241 A | | 12/1981 | Brennan ..................... | 128/743 |
| 4,990,135 A | | 2/1991 | Truesdale, Jr. ............... | 604/47 |
| 5,099,857 A | | 3/1992 | Baldo et al. ................. | 128/743 |
| 5,139,029 A | | 8/1992 | Fishman et al. ............ | 128/743 |
| 5,167,641 A | * | 12/1992 | Schmitz ...................... | 604/196 |
| 5,295,965 A | * | 3/1994 | Wilmot ....................... | 604/136 |
| 5,417,662 A | | 5/1995 | Hjertman et al. ........... | 604/117 |
| 5,665,071 A | * | 9/1997 | Wyrick ....................... | 604/134 |
| 5,671,753 A | * | 9/1997 | Pitesky ....................... | 600/556 |
| 5,779,677 A | * | 7/1998 | Frezza ........................ | 604/134 |
| 5,788,677 A | * | 8/1998 | Botich et al. ............... | 604/195 |
| 6,093,172 A | * | 7/2000 | Funderburk et al. ........ | 604/135 |
| 6,099,503 A | * | 8/2000 | Stradella ..................... | 604/135 |
| 6,203,530 B1 | * | 3/2001 | Stewart, Sr. ................ | 604/207 |
| 6,206,838 B1 | * | 3/2001 | Doll et al. .................. | 600/556 |
| 6,270,479 B1 | * | 8/2001 | Bergens et al. ............. | 604/156 |
| 6,332,871 B1 | * | 12/2001 | Douglas et al. ............. | 600/583 |
| 2002/0010456 A1 | * | 1/2002 | Sadowski et al. ........... | 604/511 |

* cited by examiner

*Primary Examiner*—Teresa Walberg
*Assistant Examiner*—Leonid M Fastovsky
(74) *Attorney, Agent, or Firm*—Pennie & Edmonds LLP

(57) ABSTRACT

An injector serving for injection of an injection fluid is described. The injector includes a housing with a contact face for during injection supporting on the skin of a person. The injection fluid is placed in a chamber in the housing which furthermore contains an injection needle placed, in a direction of activation intersecting both the at least one chamber and the contact face, displaceably in the housing from a position of rest where the needle point is in front of the at least one chamber—seen in the direction of activation—to an injection position where the point has penetrated the skin. In the point is furthermore made an eye for, at activation of the injector, receiving a fixed quantity of injection fluid during the passage of the chamber, and after this, there is placed a membrane with a slot which during the injection process fits tightly around the needle and thereby sweeps off all fluid except for the fluid in the eye. An injection can be performed with greater easiness, quickness, precision and uniformity than known so far so that a uniform basis for a medical estimate of the type of allergy and the degree of this can be obtained with e.g., an allergy test.

20 Claims, 3 Drawing Sheets

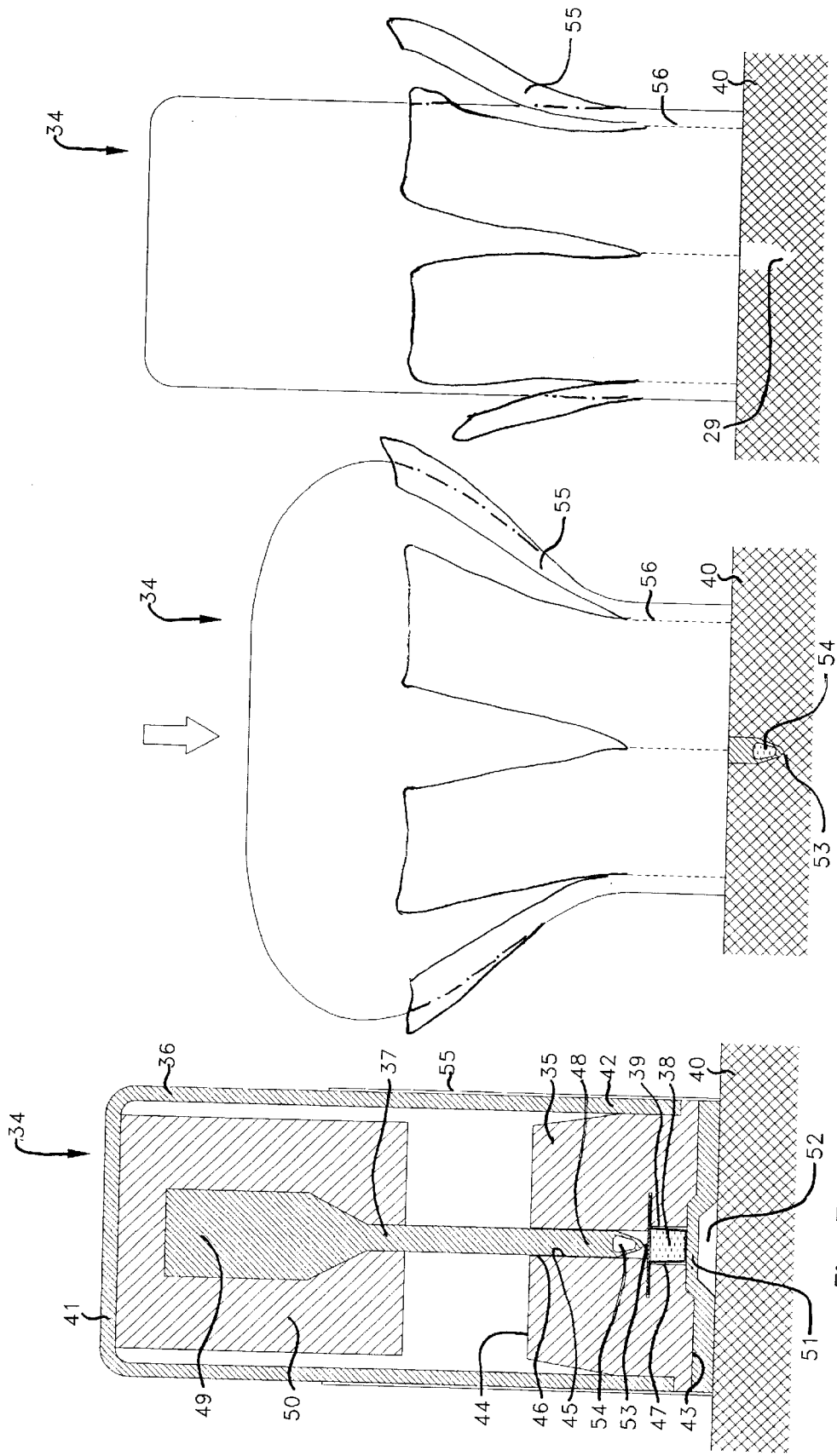

INJECTOR

This application is a continuation of the National Stage of International Application PCT/DK99/00005, filed Jan. 5, 1999, and claims priority to Danish Application No. PA 1998 0031 filed Jan. 12, 1998.

FIELD OF THE INVENTION

The invention relates to an injector for injection of at least one injection fluid and comprising a housing with a contact face for supporting on the skin, at least one chamber placed in the housing and containing an injection fluid, an injection needle which, in an activation direction intersecting both the at least one chamber and the contact face, is displaceably placed in the housing from a position of rest where the needle point is in front of the at least one chamber—seen in the activation direction—to an injection position where the point has penetrated the skin.

BACKGROUND OF THE INVENTION

In recent years, allergies have become an increasing problem especially in the Western World. Therefore, the need for being able to diagnose such diseases quickly, securely and reproducibly is growing steadily.

Conventionally, allergies are diagnosed by manually putting a number of different allergen solutions on the palm side of the patient's forearm. After this, an injection needle is pricked through the individual drops and about 1 mm into the skin so that a cavity is formed for absorbing some of the solution.

If the person is allergic to an allergen solution, the skin will after 10 to 15 minutes become red and swollen around the injection spot to an extent that depends on the quantity or the concentration of the solution that can be absorbed by the cavity. The degree of the allergic reaction can be given as a function of the extent of the swelling.

It is very difficult to dose the solution quantity with great accuracy, however, as the insertion depth of the needle and thereby the cubic capacity of the cavity depends solely on the operator's routine and skill.

With the above conventional method, the degree of the allergic reaction can therefore not be estimated with the wanted accuracy and reproducibility.

As various allergen extracts are often used at tests of an allergic reaction, there is moreover an added risk of confusing the test solutions. Furthermore, the solutions are placed directly on the skin, which opens up the possibility of contamination with allergizing agents that might give a false positive response. By using this open handling of the allergen extracts, there is furthermore a risk of the operator becoming sensitized to one of the respective allergen extracts.

An additional problem of the conventional method is the risk of infection which is present to the operator in that the injection needle remains unprotected after use.

U.S. Pat. No. 5,099,857 discloses a construction with a movable injection needle and a sealed capsule containing an allergen solution. At injection, the needle will rupture the capsule, and the solution will therefore run out and form a drop on the skin, after which the needle via the drop will penetrate the skin in the same way as mentioned above. Also in this case, the estimate of the possible skin reaction will be inaccurate. Thus, there is a need for improvements in such devices.

SUMMARY OF THE INVENTION

The present invention provides an injector of the kind mentioned in the opening paragraph, whereby it is possible to perform an injection easily, quickly, and with greater accuracy and reproducibility than known so far.

At least one recess is made in the needle point for, by activating the injector, receiving a fixed quantity of injection fluid when the recess in the needle point is passing the at least one chamber. At least one membrane, which is firmly-connected to the housing, is placed after the at least one chamber.

Thereby, it is obtained that the dosing will be very accurate and that the depth of penetration of the needle can be fixed with great accuracy by means of an integrated stop so that e.g., the degree of an allergic reaction can be determined with wanted accuracy and uniformity.

At the point, the needle will inherently have a small extension transversely. The recess in the point can therefore advantageously be an eye which easily can be made with a sufficiently large volume and which is able to receive injection fluid from the two openings of the eye at the same time.

In the membrane, there can in advance be made a slot which at injection allows passage of the needle and during this fits tightly around the needle. When the needle point passes the chamber, injection fluid is accumulated in the recess and injection fluid is moreover deposited on the needle. The latter injection fluid is swept off the needle when this needle penetrates the tight-fitting slot so that there only remains the well-defined quantity of injection fluid in the recess of the needle. At the same time, the membrane serves for preventing any injection fluid in the punctured chamber from running out on the skin.

In an advantageous embodiment, the needle forms the slot whereby complete tightness and sterility of the housing interior in the position of rest of the injector before activation is ensured.

The housing can comprise a foot with the contact face and a top which carries the needle and is displaceably placed in relation to the foot so that the injector easily can be operated by a manual pressure on the top while the foot is supported on the skin.

In the foot, there can furthermore be made a through-going channel serving both for controlling the injection needle and accommodating the membrane and the chamber.

For accurate fixing of the penetration depth of the needle, there can, on the top and foot of the housing, be made a first and a second stop respectively that join in the injection position of the needle.

According to one embodiment of the invention, both foot and top can be made of a solid material. Between these two parts, there can furthermore be placed a compression spring for returning the needle completely or partly after injection so that the risk of accidents with the needle point is eliminated.

In a second embodiment of the invention, the top of the housing can be made of an elastomeric material and the top and the bottom can be firmly connected to each other. Thereby, it is possible to maintain a sterile environment in the injector. Furthermore, the air in the housing can advantageously be used as pressure means for returning the needle after injection.

In order to prevent that the injector is activated twice by accident, the housing can be completely or partly surrounded by an of a preferably thin material, such as paper. The envelope can be arranged to be deformed or broken when the injector is activated so that it can immediately be seen if the injector has been used. The envelope can advantageously also be used for, e.g., with a specific color, indicating the respective injection fluid in the injector.

BRIEF DESCRIPTION OF THE DRAWINGS

The invention will be explained in greater detail below, describing only exemplary embodiments with reference to the drawing.

FIG. 7 is an axial sectional view from the side of a second embodiment of an injector according to the invention in a position of rest.

FIG. 8 is a side elevational view of the injector in FIG. 7 in a position of injection.

FIG. 9 is the injector in FIG. 8 after injection.

DETAILED DESCRIPTION OF PREFERRED EMBODIMENTS

Figure 1:
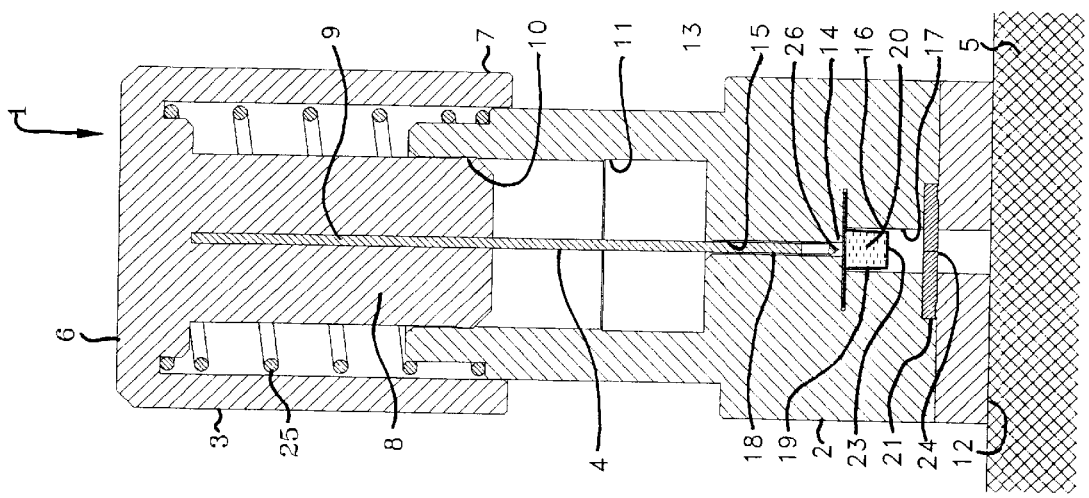
FIG. 1 is an axial sectional view from the side of a first embodiment of an injector according to the invention in a position of rest.
Figure 2:
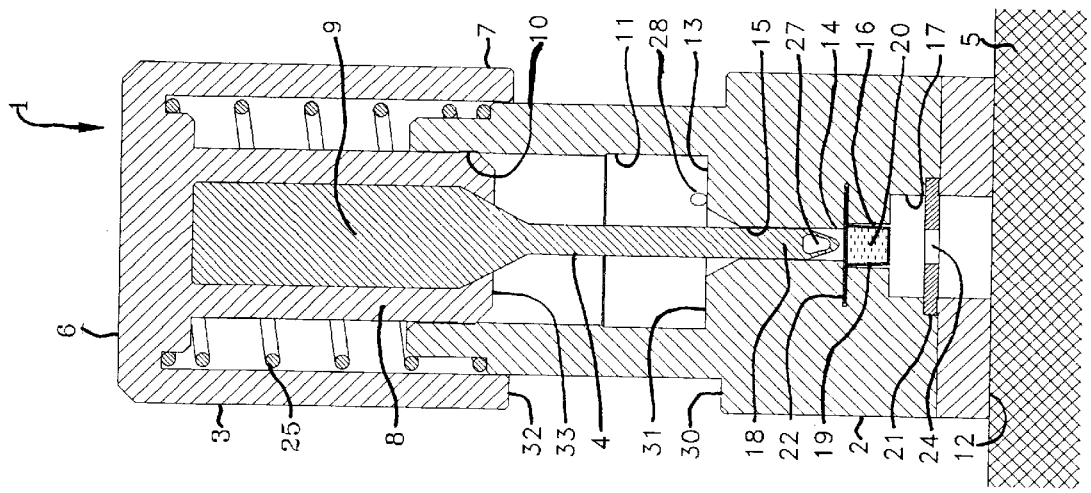
FIG. 2 shows the injector in FIG. 1 but turned 90° about the axis.

The invention is described in the following on the assumption that the injector is employed for an allergy test.

The orientation in space of the different components of the injector is furthermore based on the position of the injector in the drawing. In this connection, it should be noted that the injector just as well can be employed in any other appropriate position.

For the sake of clarity, the injector is shown on a large scale in the drawing. In practice, it would have a diameter of e.g., 10 mm and a height of e.g., 25 mm.

In the shown embodiment, the injector is formed as a cylinder with a circular cross section. Within the scope of the invention, the cross section can however also be polygonal or have any other appropriate configuration.

The injector shown in FIGS. 1 to 6 is designated generally by the reference numeral 1. The main components of the injector are a foot 2, a top 3, and an injection needle 4. The injector is, in the shown case, employed for injection in an only fragmentarily indicated piece of skin 5.

The injector according to the invention must only be used once. After use, it should be discarded. It is therefore important that the injector can be manufactured at a reasonable price. The top and foot of the injector are therefore advantageously made by pressure die-casting in an appropriate plastic. However, metal, glass and other materials that comply with the demand for adequate rigidity and shape-permanence can also be used.

The top 3 is shaped as a cap with a surface 6 and a hanging skirt 7 for receiving the foot 2 with a sliding fit. Internally, the top has a central pin 8. An upper part 9 of the needle 4 is molded into this pin 8 or fastened to it by means of e.g., a press fit.

The foot 2 has an upper blind hole 10 for, with a relatively tight sliding fit, receiving the central pin 8 of the top. At the bottom, the blind hole 10 has a clearance 11.

The foot 2 has a contact face 12 with which the injector supports on the skin 5 during injection. Between the contact face 12 and the bottom 13 of the blind hole 10, a central channel 14 is extending that is stepped in three sections 15, 16 and 17.

A lower part 18 of the needle 4 is, with a sliding fit, received in the upper section 15 of the channel. Thereby this section 15 serves for guiding the needle during injection.

In the middle section 16 which has a larger cross section than the upper section 15 is placed a capsule 19 containing an injection fluid 20.

In the lower section 17 is placed a tight-fitting, elastomeric membrane 21 of e.g., rubber.

The capsule 19 is made of a relatively thin and easily breakable plastic which before use hermetically encapsulates the fluid 20. The capsule has an upper wall 22 and a lower wall 23.

In the membrane, for example, there may be made a slot 24 which can be seen crosswise in FIG. 1 and lengthwise in FIGS. 2 to 6.

Between the foot 2 and the top 3 is furthermore placed a compression spring 25.

The needle 4, which among persons skilled in the art also is known as a lancet, is made of e.g., steel or a strong, rigid plastic. In the shown case, the needle has a rectangular cross section with two relatively narrow sides and two relatively broad sides. At the bottom of the needle is made a sharp point 26 with an eye 27 extending through the point and ending in the two broad sides.

In the foot 2 is furthermore made a ventilation hole 28 for equalising the pressure in the blind hole 13 of the foot when the injector is activated.

During storing, the injector is sterilely packed in a packing (not shown) of e.g., plastic film. When the injector is to be used, the packing is broken, and the injector is placed on the skin 5 as shown in FIGS. 1 to 6.

In FIG. 1, the injector is seen in its starting position from the narrow side of the needle and in FIGS. 2 to 6, from the broad side of the needle. As shown, the needle point 25 is, in the starting position, at a small distance up above the upper wall 22 of the capsule 19.

Figure 3:
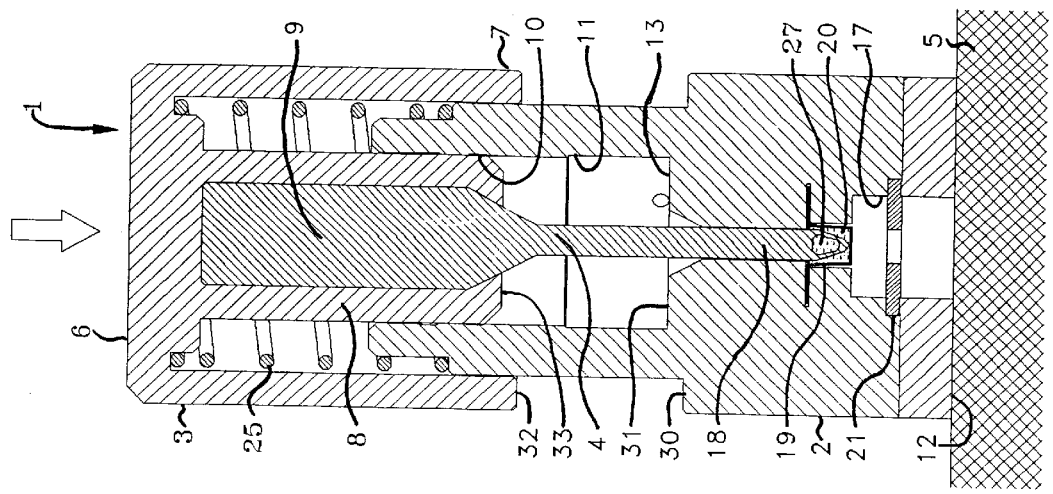
FIG. 3 shows the injector in FIG. 2 in a first activation phase.

In FIG. 3, the top 2 is, with a finger indicated with the shown arrow, pressed downwards a distance towards the effect of the spring power of the compression spring 25. During this, the needle point has broken through the upper wall 22 of the capsule 19, and the eye 27 of the point 26 is now in the fluid 20. At this time, the eye is filled with fluid which at the same time wets the rest of the surface of the point.

Figure 4:
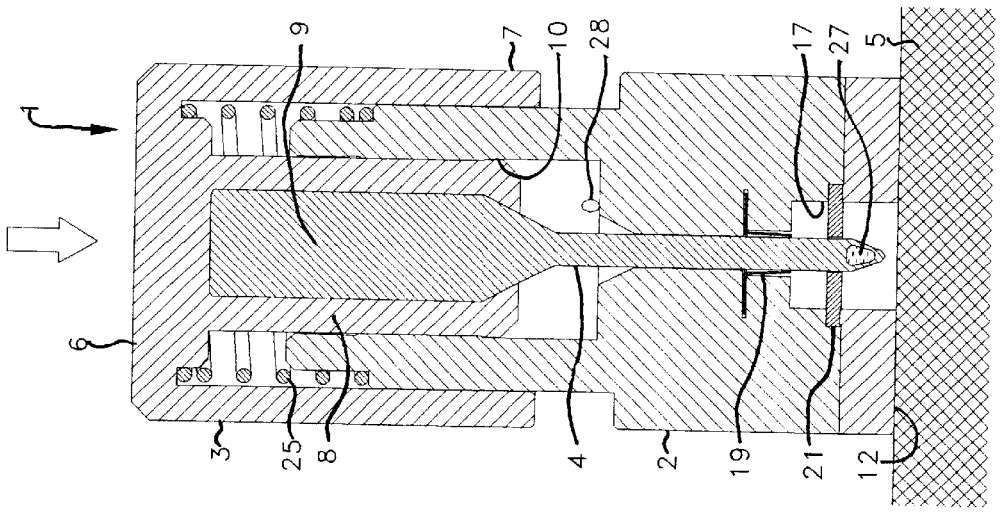
FIG. 4 shows the injector in FIG. 3 in a second activation phase.

In FIG. 4, the needle point 26 with the fluid-filled eye 27 has penetrated the lower wall 23 of the capsule 19 and further through the membrane 21 slot 24 which during the membrane is squeezed tightly together around the point by the elastic power generated in the membrane when the slot is opened.

Thereby, all fluid is swept off the needle and its point except for the fluid in the eye 27. As the slot of the membrane fits tightly around the needle, the swept-off fluid and fluid which has run out through the broken lower wall 23 of the capsule by itself remain on the top side of the membrane.

The fluid in the eye will not come into contact with the wall of the slot 24, however, and it therefore avoids being mechanically swept off during the passage of the slot of the membrane. After passage, the surface tension of the fluid makes sure that the fluid is kept back in the eye.

Figure 5:
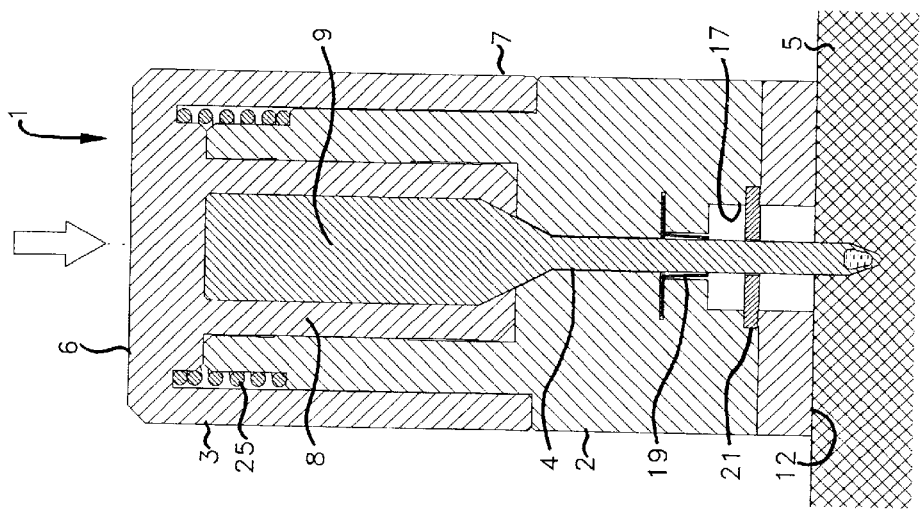
FIG. 5 shows the injector in FIG. 3 in a position of injection.

During the final injection shown in FIG. 5, a completely accurately fixed quantity of fluid is therefore led into the cavity 29 formed in the skin 5 during the penetration of the needle.

The penetration depth of the needle is furthermore fixed completely accurately by means of concurrent, upper stop faces 30 and 31 on the foot 2 and lower stop faces 32 and 33 on the top 3, respectively. When the respective stop faces on the two parts 2 and 3 of the injector meet, the needle point is in a wanted depth of penetration corresponding to the distance from the contact face 12 of the foot.

Figure 6:
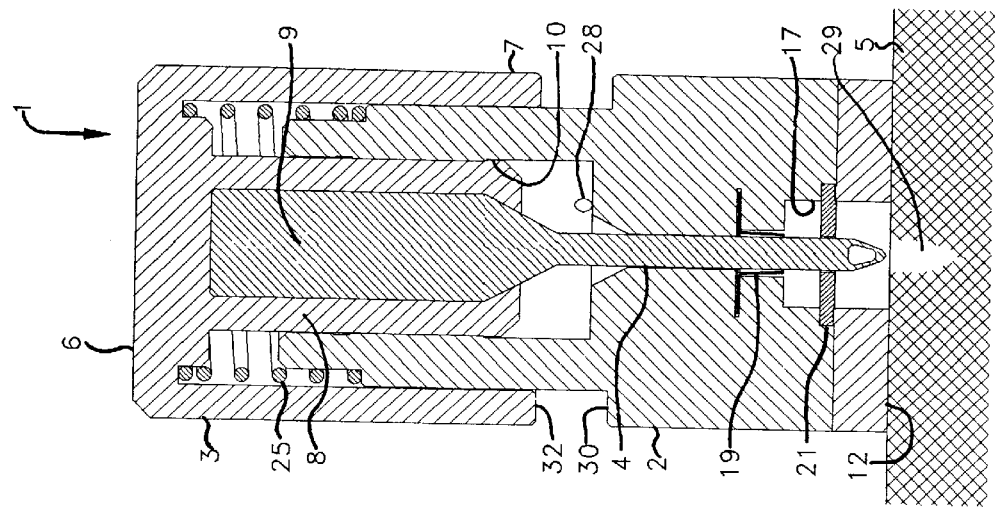
FIG. 6 shows the injector in FIG. 3 after injection.

In FIG. 6, the injection is completed. The fluid in the eye 27 has been received by the cavity 29 while the compression spring has pulled the point free of the cavity and a distance up above the contact face 12 of the foot so that the patient or the operator will not subsequently unintentionally be pricked by the point.

As the central pin 8 of the top fits rather tightly in the blind hole 10 of the foot owing to the tight sliding fit between these two parts, the top is however stopped before it returns completely to the starting position so that it is possible to see whether the injector has been used or not.

After use, the injector is removed for depositing and/or destruction. After a prefixed period of time has passed, typically 10 to 15 min., the extent of the swelling which the injection fluid might have caused is measured. The measured value can be used for estimating the degree of the allergic reaction to the respective injection fluid.

The medical estimate of the allergy can however be made with far greater reliability than up till now as the injections are now each time carried out with the exact same quantity of injection fluid and exact same depth of injection. The measured results are therefore independent of the operator and coincidences. Instead, completely comparable results are obtained.

FIGS. 7, 8, and 9 show a second embodiment of the injector according to the invention. This injector, designated generally by the reference numeral 34, is mainly arranged in the same way as the injector shown in FIGS. 1 to 6 with a foot 35, a top 36, and a needle 37. Correspondingly, the injector is assumed to be employed for an allergy test with an injection fluid 38 placed in a capsule 39 and to be injected in an only fragmentarily shown piece of skin 40.

The top is made of an elastomer, such as rubber, and it is shaped as a cap with a bottom 41 and a hanging skirt 42.

The foot, which is made of a rigid plastic or another rigid, solid material, has an underside 43 and an opposite top side 44. Between the two sides 43 and 44 of the foot, a central channel 45 is extending, which is stepped in an upper and a lower section 46 and 47.

A lower part 48 of the needle 37 is, with a sliding fit, received in the upper section 46 of the channel, thereby this section serves for guiding the needle during injection. An upper part of the needle 37 is moulded into a plastic plug 50 attached with e.g., adhesive on the inside of the bottom 41 of the top.

As shown, the capsule 39 with the injection fluid 38 is placed in the lower section 47 of the channel 45.

An elastomeric membrane of e.g., rubber is attached by means of e.g., adhesive on the underside 43 of the foot 35. In this case, a slot has not been pre-made in the membrane.

The shown membrane covers the entire underside 43 on the foot 35 but can alternatively be extending over a small part of this underside. The membrane has a central recess 51 on the underside.

The foot 35 and the top 36 are tightly joined by means of e.g., bonding or hot welding, and as can be seen, the interior of the injector is thus hermetically isolated from the outer surroundings. Thereby, the advantage is obtained in that the active parts of the injector can be stored sterilely without individual packing.

In principle, the needle 37 is made in the same way as the one in FIGS. 1 to 6 with a point 53 and an eye 54.

In the starting position shown in FIG. 7, the needle point 53 is just above the capsule 39 which again is abutting on the top side of the membrane 51 in the area above its central recess 52.

In the shown case, the injector is surrounded by a thin-walled envelope 55 with a number of vertically oriented breaking lines 56 (FIGS. 8 and 9). The envelope can with color, text or another kind of indication indicate the type and effect of the respective fluids.

In FIG. 8, the top 36 is with a finger, which is indicated by the shown arrow, pressed down to its injection position while running through the same processes as the ones described under the first embodiment, and these will therefore not be mentioned any further here.

As the membrane in this case is not provided with a slot in advance, however, the needle itself will cut a tightly-fitting slot in the membrane when it penetrates through this on activation of the injector.

During the depression, the elastomeric top 36 bulges and thereby bursts the envelope 55 along at least some of the breaking lines. The envelope deformed in this way thus clearly shows that the injector has been used so that it is ensured that the injector will not unintentionally be reused.

The envelope 55 can be made of paper, plastic, or metal. It is an advantage when the employed material is not very elastic so that the envelope will remain standing in its burst position, and thereby clearly indicate that the injector has been used.

When the top is pressed down, the trapped air is compressed in the top. When the top is let go after injection, the air expands and thereby presses, as shown in FIG. 9, the top back to its starting position with the needle point retracted.

An injection can be performed with greater easiness, quickness, precision and uniformity than known so far with both of the above embodiments of an injector according to the invention.

The invention is described above and shown in the drawing on the assumption that the injector is to be employed for an allergy test. In addition, the injector can within the scope of the invention be employed for many other purposes where an exact quantity of a fluid is required injected at a precise depth.

In the channel of the injector can furthermore be placed two or more capsules on top of each other. An upper capsule can thus be filled with a lyophilised substance and an subjacent capsule with a liquid for dissolving the substance.

Between two capsules of this kind can furthermore be placed an additional membrane.

The described injectors can form the individual components of a large unit. The unit can e.g., comprise twelve injectors containing ten different allergen extracts respectively, and a positive and a negative control. The injectors can preferably be placed in a row on e.g., a strip of plastic, which furthermore can be arranged to be easily detachably stuck on e.g., an arm.

The injector can however also be employed one by one or in sets stored in a box.

What is claimed is:

1. An injector for injection of at least one injection fluid, the injector comprising a housing with a contact face for supporting the injector on the skin;

at least one chamber placed in the housing and containing the at least one injection fluid;

an injection needle comprising a needle point displaceably placed, in a direction of activation intersecting both the at least one chamber and the contact face, in the housing from a position of rest where the needle point is in front of the at least one chamber—seen in the direction of activation—to an injection position where the point has penetrated the skin, wherein at least one recess is present in the needle point for receiving a fixed quantity of injection fluid when the injector is activated and when the recess in the needle point is passing the at least one chamber; and at least one membrane connected to the housing and placed behind said at least one chamber.

2. The injector according to claim 1, wherein the at least one recess in the point is an eye.

3. The injector according to claim 1, wherein the at least one membrane has a pre-made slot arranged to allow passage of the needle therethrough and during this passage the slot fits tightly around the needle.

4. The injector according to claim 3, wherein the slot is made during the passage of the needle through the at least one membrane so as to fit tightly around the needle.

5. The injector according to claim 1, wherein the housing comprises a foot with the contact face, which foot supports the injector on the skin, and a top connected with the injection needle, which top is displaceable in relation to the foot.

6. The injector according to claim 5, wherein the foot is penetrated by a channel that guides the injection needle and receives the membrane and the chamber.

7. The injector according to claim 6, wherein the channel is arranged at a right angle to the contact face.

8. The injector according to claim 5, wherein a first stop and a second stop are made on the top and the foot of the housing, respectively, for an injection while concurrently fixing the injection position.

9. The injector according to claim 5, wherein the top of the housing comprises a solid material, and the injector further comprises a compression spring positioned between the top and the foot.

10. The injector according to claim 5, wherein the top of the housing comprises an elastomeric material, and wherein the top and the foot are interconnected.

11. The injector according to claim 1, wherein the housing is at least partly surrounded by an envelope which is arranged to be deformed or broken when the injector is activated.

12. The injector according to claim 11, wherein the housing is completely surrounded by the envelope.

13. An injector for injection of at least one injection fluid, said injector comprising a housing with a contact face for supporting the injector on the skin;

at least one chamber placed in the housing and containing the at least one injection fluid;

an injection needle comprising a needle point and at least one recess in the needle for receiving a fixed quantity of injection fluid when the needle passes through the at least one chamber; and at least one membrane connected to the housing and positioned between the at least one chamber and the contact face, wherein the needle point is positioned and configured to be displaced from a rest position through the at least one chamber and through the at least one membrane to an injection position where the needle point has been displaced beyond the contact face.

14. The injector of claim 13 wherein the housing comprises a foot with the contact face and a channel passing therethrough, and a top slidably connected to the foot and capable of being displaced toward the contact face, wherein the needle is secured to the top and is sized and positioned to pass through the channel, and wherein the at least one chamber is in the channel at a position between the needle point and the membrane.

15. The injector of claim 14 wherein at least one recess in the needle is an eye.

16. The injector of claim 14 wherein the at least one membrane has a pre-made slot sized and positioned to provide wipe the injection fluid from the outside of the needle as the needle passes therethrough.

17. The injector of claim 14 wherein the channel is arranged at a right angle to the contact face.

18. The injector of claim 14 wherein the top further comprises at least one stop which contacts the foot when the injector is in the injection position.

19. The injector of claim 18 further comprising a compression spring positioned between the top and the foot.

20. The injector of claim 18 further comprising an envelope attached to the housing, wherein the envelope is configured and positioned to be deformed or broken when the injector is activated from a rest position to an injection position.

* * * * *